United States Patent
Kaji et al.

(10) Patent No.: US 7,259,213 B2
(45) Date of Patent: Aug. 21, 2007

(54) INDOLE RESINS EPOXY RESINS AND RESIN COMPOSITIONS CONTAINING THE SAME

(75) Inventors: Masashi Kaji, Tokyo (JP); Hisashi Yamada, Tokyo (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 332 days.

(21) Appl. No.: 10/504,272

(22) PCT Filed: Feb. 10, 2003

(86) PCT No.: PCT/JP03/01380

§ 371 (c)(1),
(2), (4) Date: Jan. 25, 2005

(87) PCT Pub. No.: WO03/068837

PCT Pub. Date: Aug. 21, 2003

(65) Prior Publication Data

US 2005/0131167 A1    Jun. 16, 2005

(30) Foreign Application Priority Data

Feb. 12, 2002  (JP) ............... 2002-034302
Nov. 11, 2002  (JP) ............... 2002-327080

(51) Int. Cl.
| | |
|---|---|
| C08G 12/26 | (2006.01) |
| C08G 59/02 | (2006.01) |
| C08G 63/00 | (2006.01) |
| C08L 61/06 | (2006.01) |
| C07D 209/04 | (2006.01) |

(52) U.S. Cl. .............. 525/509; 525/481; 525/489; 525/507; 525/510; 525/490; 528/246; 528/248; 528/250; 528/420; 548/455

(58) Field of Classification Search ............ None
See application file for complete search history.

(56) References Cited

U.S. PATENT DOCUMENTS 6,204,274 B1 * 3/2001  Kelly et al. ............ 514/322

FOREIGN PATENT DOCUMENTS

JP    11-140166 A1    5/1999

OTHER PUBLICATIONS

International Search Report for PCT/JP03/01380 mailed on May 20, 2003.
J. Bergman, "Condensation of Indole and Formaldehyde in the Presence of Air and Sensitizers", Tetrahedron, Jul. 1970, vol. 26, No. 13, pp. 3353 to 3355.
Jason Bloxham et al., "Synthesis and Solid State Structures of N, N'-linked Carbazoles and Indoles", Tetrahedron, May 2002, vol. 58, No. 19, pp. 3709 to 3720, pp. 3710.
International Preliminary Examination Report for PCT/JP2003/001380 mailed on Oct. 28, 2004.
Julia et al., Bull. Soc. Chim. Fr., 1964, pp. 1946-1953, XP008054613, pp. 1948, column 1, line 1; example 6.
Supplementary European Search Report dated Nov. 2, 2005.

* cited by examiner

*Primary Examiner*—David J. Buttner
(74) *Attorney, Agent, or Firm*—Rader, Fishman & Grauer PLLC (57) ABSTRACT

This invention relates to epoxy resins containing indole as structural unit, indole resins and resin compositions containing said epoxy resins and indole resins useful for applications such as laminating, molding, casting and adhesion on account of their excellent fire retardance, adhesiveness, moisture resistance and heat resistance.

The indole resins of this invention and the epoxy resins obtained therefrom are represented by the following general formulas I and II

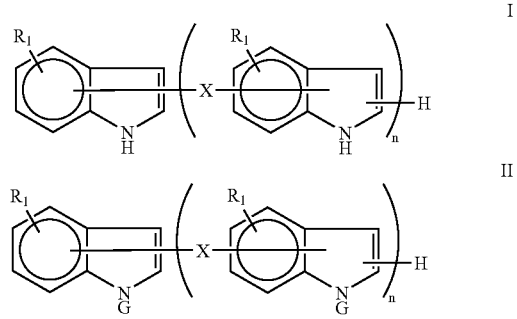

wherein $R_1$ is H, alkyl or the like, X is a crosslinking group represented by —$C(R_2R_3)$— or $C(R_4R_5)$—Ar—$C(R_4R_5)$— (wherein $R_2$-$R_5$ are H, alkyl or the like and Ar is a benzene or biphenyl ring), G is glycidyl group and n is an integer of 1-20.

6 Claims, 4 Drawing Sheets

INDOLE RESINS EPOXY RESINS AND RESIN COMPOSITIONS CONTAINING THE SAME

FIELD OF TECHNOLOGY

This invention relates to indole resins which are useful as epoxy resin intermediates, curing agents and the like. Furthermore, thus invention relates to epoxy resins derivable from indole resins, epoxy resin compositions and cured products of said compositions.

BACKGROUND TECHNOLOGY

Epoxy resins are used industrially in a wide variety of applications and their performance requirements are becoming increasingly more exacting in recent years. For example, resin compositions containing epoxy resins as main ingredients have been used typically as materials for encapsulating semiconductors and there is currently a demand for materials of improved solder heat resistance as an increase in the scale of integration of semiconductor devices has caused the packages to become larger in area and smaller in thickness and the packaging technology to shift to surface mounting. In consequence, there is a strong demand for encapsulating materials of reduced moisture absorption and improved adhesiveness at the interface of materials of different kind such as lead frames and chips. The same holds for materials for circuit boards and there is a demand for materials with properties of not only reduced moisture absorption, higher heat resistance and improved adhesiveness from the viewpoint of improving solder heat resistance but also reduced dielectric properties from the viewpoint of reducing dielectric loss. Moreover, in recent years, there is a trend toward elimination of halogen-based fire retardants from the viewpoint of reducing environmental load and this has created a demand for curing agents of improved fire retardance.

To meet these requirements, various novel structures have been investigated for epoxy resins which constitute the main ingredients on the side of epoxy resin suppliers and, concurrently, curing agents are receiving investigation.

As for base resins, there is a strong demand for improvements in moisture resistance, heat resistance and adhesiveness to metallic base materials.

However, none of the epoxy resins known thus far has satisfied the aforementioned requirements. For example, as is generally known, bisphenol type epoxy rest have found wide use as they are liquid at normal temperature, easy to work with and readily miscible with curing agents, additives and the like, but they face problems with resect to heat resistance and moisture resistance. Novolac type epoxy resins are known for their improved heat resistance, but they still have problems with respect to moisture resistance, adhesiveness and the like. Moreover, the conventional epoxy resins whose main skeleton is made up of hydrocarbons alone are completely devoid of fire retardance.

One of the measures known to improve fire retardance without the use of halogen-based fire retardants is to acid phosphate ester-based fire retardants. However, the addition of phosphate ester-based fire retardants fails to achieve sufficient moisture resistance. Furthermore, phosphate esters undergo hydrolysis in an environment of high temperature and moisture and lower the reliability of epoxy resins as insulating materials.

Studies are underway on the curing agents of epoxy resins. A candidate is naphthalene reins and an application of naphthol-aralkyl resins as encapsulants of semiconductors is disclosed in JP5-109934-A. Naphthol-aralkyl resins have excellent properties of low moisture absorption, low thermal expansion and the like, but show poor curability. Curing agents having a biphenyl structure are proposed in JP11-140166-A and described to be effective for improving fire retardance, but they are defective in curability. Moreover, since naphthalene-based resins and biphenyl-based resins have backbones made up of hydrocarbons alone, they were unable to manifest sufficient fire retardance.

DISCLOSURE OF THE INVENTION

An object of this invention is to provide indole reins useful as intermediates of epoxy resins. Another object is to provide indole resins useful as curing agents and the like of epoxy resin compositions. A further object is to provide epoxy resin compositions which contain said indole reins, yield cured products of good moldability and excellent properties with respect to moisture absorption, heat resistance, adhesiveness, fire retardance and the like and are useful as encapsulants of electric and electronic parts and as materials of circuit boards and to provide said cured products. A further object is to provide phenolic resin compositions which contain said indole resins and are useful as curing agents of epoxy resins.

A further object of this invention is to provide epoxy resins which show excellent fire retardance, moisture resistance, heat resistance and good adhesion to metallic base materials and are useful for such applications as laminating, molding, casting and adhesion and to provide a method for preparing said epoxy resins. A further object is to provide epoxy rein compositions which contain curing agents and said epoxy resins and to provide cured products of said epoxy resin compositions.

This invention relates to indole resins represented by the following general formula I. Furthermore, this invention relates to epoxy resins represented by the following general formula II.

In general formulas I and II, X is a crosslinking group represented by the following general formula (a) or (b)

(wherein $R_2$ and $R_3$ are hydrogen or hydrocarbon group containing 1-6 carbon atoms, $R_4$ and $R_5$ are hydrogen or methyl group and m is 1 or 2) and n is an integer of 1-20.

In general formula I, $R_1$ is hydrogen, hydroxyl group, hydrocarbon group containing 1-8 carbon atoms, alkoxy group containing 1-6 carbon atoms or halogen. In general formula II, $R_1$ is hydrogen, hydrocarbon group containing 1-8 carbon atoms, alkoxy group containing 1-6 carbon atoms, glycidyloxy group or halogen and G is glycidyl group.

This invention further relates to a method for preparing the aforementioned epoxy resins which comprises reacting said indole resins with epichlorohydrin in the presence of an alkali metal hydroxide.

The indole resins and epoxy resins of this invention are represented respectively by the general formulas I and II and the epoxy resins are obtained by epoxidizing the indole resins with epichlorohydrin. Therefore, X and n are common to general formulas I and II. However, n may change to some extent occasionally due to secondary reactions and the like in the course of epoxidation. In the case where $R_1$ in general formula I is hydroxyl group, $R_1$ in general formula II becomes glycidyloxy group; in other cases, $R_1$ is common to general formulas I and II.

The group X in general formulas I and II is a crosslinking group that links indole rings and is represented by the aforementioned general formula (a) or (b). In general formula (a), $R_2$ and $R_3$ are independently hydrogen or hydrocarbon group containing 1-6 carbon atoms. The hydrocarbon group here is exemplified by methyl, ethyl, n-propyl, isopropyl butyl, amyl and phenyl.

A preferable crosslinking group represented by general formula (a) is —CH($R_2$)— (wherein $R_2$ is hydrogen or hydrocarbon group containing 1-6 carbon atoms). Concrete examples of this group are methylene, ethylidene, isopropylidene and phenylethylene.

In general formula (b), $R_4$ and $R_5$ are independently hydrogen or methyl group and m is an integer of 1 or 2. Examples of preferable crosslinking groups represented by general formula (b) are p-xylylene, m-xylylene, 1,4-bisethylidenephenylene, 1,3-bisethylidenephenylene, 1,4-bisisopropylidenephenylene, 1,3-bisisopropylidenephenylene, 4,4'-bismethylenebiphenyl, 3,4'-bismethylenebiphenyl, 3,3'-bismethylenebiphenyl, 4,4'-bisethylidenebiphenyl, 3,4'-bisethylidenebiphenyl, 3,3'-bisethylidenebiphenyl, 4,4'-bisisopropylidenebiphenyl, 3,4'-bisisopropylidenebiphenyl, and 3,3'-bisisopropylidenebiphenyl.

The number of repeating units or n is in the range of 1-20 and it is preferably in the range of 1-5 on the average.

In the general formulas I and II, $R_1$ is hydrogen, hydrocarbon group containing 1-8, preferably 1-7, carbon atoms, alkoxy group containing 1-6 carbon atoms, hydroxyl group (glycidyloxy group in the case of general formula II) or halogen.

The hydrocarbon group here is exemplified by methyl, ethyl, n-propyl, isopropyl, allyl, propargyl, butyl, n-amyl, sec-amyl, tert-amyl, cyclohexyl, phenyl and benzyl. The alkoxy group is exemplified by methoxy, ethoxy, vinyloxy, isopropoxy, allyloxy, propargyloxy, butoxy and phenoxy and the halogen by F, Cl and Br.

The indole reins of this invention are represented by the general formula I and n is an integer in the range of 2-20, preferably 2-15. The indole resins in question may be a single compound or a mixture of compounds with n in the range of 2-20. In the cases where the softening point of the indole resins is in the range of 40-200° C., n is an average number of repeating units (number average) in the range of 1-20. The softening point of the indole resins is 40-200° C., preferably 50-160° C., more preferably 60-120° C. The softening point referred to here is the one determined in accordance with the ring and ball method specified by JIS K-6911. When incorporated in epoxy resins, indole resins with a softening point lower than this cause degradation of the heat resistance of the cured products while those with a softening point higher than this reduce the fluidity during molding. A desirable average number of repeating units in this case is decided by the aforementioned softening point and it is preferably in the range of 1.2-15, more preferably 1.5-10. The indole resins of this invention include the ones which are obtained by the reaction of 1 mole of an indole with 0.1-9 moles of an aldehyde in the presence of an acid catalyst and show a softening point in the range of 40-200° C.

The location of the crosslinking group X on the indole ring in the general formula I is not restricted and a hydrogen atom at any of positions 1 to 7 can be replaced by the crosslinking group to link indole rings. In the cases where the hydrogen atom at potion 1 is replaced by the crosslinking group, H of >NH disappears. It is not necessary for all the hydrogen atoms at position 1 of the indole ring to remain intact; however, complete replacement of all the hydrogen atoms at position 1 prevents the indole resins of this invention from manifesting their function as a curing agent. It is therefore desirable that 10% or more of the hydrogen atoms at position 1 remains intact. If the preparation is conducted according to a normal procedure, the probability of replacing respective hydrogen atom at positions 1-7 is 1/7 and this means that at least 50% of the hydrogen atom at position 1 remains intact. It is possible to estimate by NMR measurement how many hydrogen atoms of the >NH group remain.

The indole resins of this invention can be synthesized by the reaction of an indole with a crosslinking agent that gives the crosslinking group represented by the aforementioned general formula (a) or (b). A crosslinking agent represented by the following general formula (c) or (d)

(wherein $R_2$-$R_5$ and m are as defined in general formula (a) or (b) and Y is hydroxyl group, halogen or alkoxy group containing 1-6 carbon atoms) can serve as such crosslinking agent.

Crosslinking agents giving the crosslinking group represented by general formula (a) include aldehydes or ketones represented by the aforementioned general formula (c). Here, $R_2$ and $R_3$ are as defined in general formula (a). Concrete examples of such aldehydes and ketones are formaldehyde, acetaldehyde, propylaldehyde, butyraldehyde, amylaldehyde, benzaldehyde and acetone and formaldehyde is preferred. Formaldehyde as a raw material for the reaction is used preferably in the form of formalin, paraformaldehyde, trioxane and the like.

Crosslinking agents giving the crosslinking group represented by general formula (b) include aromatic crosslinking agents represented by the aforementioned general formula (d). Here, $R_4$ and $R_5$ are as defined in general formula (b). Concrete examples are xylylene glycol alkyl ethers of xylylene glycol and xylylene dichloride.

The crosslinking agent is used in an amount of 0.1-0.9 mole, preferably 0.2-0.8 mole, per 1 mole of an indole. The molecular weight of oligomers can be adjusted by changing this molar ratio. When the synthesis is carried out at a molar ratio lower than this, the amount of the unreacted indole increases and the productivity of indole resins drops; the product indole resins have a lower softening point or molecular weight and, when used as a curing agent for epoxy resins, the cured product deteriorates in heat resistance. On the other hand, the synthesis conducted at a molar ratio higher than this raises the softening point of indole resins and, on occasions, the indole resins undergo gelation in the course of synthesis. The indole resins with a desirable number of repeating units (n) can be separated by such means as column chromatography liquid chromatography, GPC and solvent partition.

An essential ingredient of monomers to be used in the preparation of the indole reins of this invention is an indole compound and a substituted indole can be used in addition to indole. The substituent group here is represented by the aforementioned group $R_1$ (excluding H): F, Cl or Br as halogen; methoxy, ethoxy, vinyloxy, isopropoxy, allyloxy, propargyloxy, butoxy or phenoxy as alkoxy; methyl, ethyl, vinyl, ethynyl, isopropyl, allyl, propargyl, butyl, amyl, phenyl or benzyl as hydrocarbon group. Although a variety of indole derivatives having 1 or more substituents and indole itself can be used, it is preferable to use an indole having one $C_{1-3}$-alkyl group and indole itself.

It is possible to have a phenol coexist with an indole in the monomers to be used for the preparation of the indole resins of this invention. Examples of such phenol are phenol, alkylphenols such as cresols and xylenols, naphthols, naphthalenediols, bisphenols such as bisphenol A and bisphenol F, and polyfunctional phenolic compounds such as phenol novolac and phenol-aralkyl resins. These monomers can be used singly or as a mixture of two kinds or more. However, the properties of the cured products obtained by incorporation of the indole resins improve as the content of indole skeleton in the indole resins increases and the addition of the aforementioned phenol although not specifically restricted, is normally kept at 50 wt % or less, preferably 30 wt % or less. In the cases where a phenol coexists in the monomers, indole resins mixed with resins containing the phenol as a part of the constituents and phenolic resins are obtained in addition to the indole resins represented by general formula I. In this case, the aforementioned amount of aldehyde is used per 1 mole of the sum of indole and phenol.

The reaction for the synthesis of indole resins can be carried out in the presence of an acid catalyst. The acid catalyst is properly selected from the known inorganic and organic acids; for example, mineral acids such as hydrochloric acid, sulfuric acid and phosphoric acid, organic acids such as formic acid, oxalic acid, trifluoroacetic acid, p-toluenesulfonic acid, dimethylsulfuric acid and diethylsulfuric acid, Lewis acids such as zinc chloride, aluminum chloride, iron chloride and boron trifluoride and solid acids such as ion exchange resin, activated clay, silica-alumina and zeolite.

The reaction is normally carried out at 10-250° C. for 1-20 hours. It is allowable to use a solvent in the reaction; for example, an alcohol such as methanol, ethanol, propanol, butanol, ethylene glycol, Methyl Cellosolve and Ethyl Cellosolve, a ketone such as acetone, methyl ethyl ketone and methyl isobutyl ketone, an ether such as dimethyl ether, diethyl ether, diisopropyl ether, tetrahydrofuran and dioxane and an aromatic compound such as benzene, toluene, chlorobenzene and dichlorobenzene.

Upon completion of the reaction, the indole may occasionally remain unreacted in the product indole resins. The residual unreacted indole is usually removed from the system by such means as distillation under reduced pressure and solvent partition. The amount of unreacted indole is desirably kept low in the indole resins and it is normally 5 wt % or less, preferably 3 wt % or less, more preferably 1 wt % or less. If the indole remains in a large amount, it evaporates during the preparation of molded articles thereby reducing the molding efficiency and causing voids in the molded articles. Moreover, the molded articles deteriorate in fire retardance.

The indole resins of this invention are used as intermediates for epoxy resins and also they are mixed with other resins to formulate resin compositions. Preferably, the indole reins can be used to constitute an ingredient of phenolic resin compositions or epoxy resin compositions. Moreover, the reaction of the indole reins with halogenated alkyl compounds, halogenated alkenyl compounds, epihalohydrins and the like can yield modified indole resins in which a part or the whole of the hydrogen atoms located on the nitrogen atom (>NH) in the indole resins is substituted by alkyl, alkenyl or glycidyl group. The indole resins of this invention perform excellently as a curing agent for epoxy resins and they can be used as such.

In the cases where the indole resins of this invention are mixed with phenolic resins to formulate phenolic resin compositions, the content of the indole resins is kept in the range of 2-200 parts by weight, preferably 5-100 parts by weight, more preferably 10-80 parts by weight, per 100 parts by weight of the phenolic resins. A content lower than this improves little the moisture absorption, heat resistance, adhesion, fire retardance and the like while a content higher than this increases the viscosity thereby deteriorating moldability.

The phenolic reins here mean all the compounds possessing two or more hydroxyl groups in the molecule; for example, dihydric phenols such as bisphenol A, bisphenol F, bisphenol S, fluorenebisphenol, 4,4'-biphenol 2,2'-biphenol, hydroquinone, resorcin and naphthalenediol and trihydric and higher phenols such as tris(4-hydroxyphenyl)methane, 1,1,2,2-tetrakis(4-hydroxyphenyl)ethane, phenol novolac, o-cresol novolac, naphthol novolac and poly(vinyl phenol). Examples further include polyhydric phenolic compounds synthesized by the reaction of a phenol or dihydric phenol with a crosslinking agent; a phenol or dihydric phenol is selected from phenols, naphthols, bisphenol A, bisphenol F, bisphenol S, fluorenebisphenol, 4,4'-biphenol, 2,2'-biphenol, hydroquinone, resorcin and naphthalenediol and a crosslinking agent is selected from formaldehyde, acetaldehyde, benzaldehyde, p-hydroxybenzaldehyde, p-xylylene glycol, p-xylylene glycol dimethyl ether, 4,4'-dimethoxymethylbiphenyl, 4,4'-dimethoxymethyldiphenyl ether, divinylbenzenes, divinylbiphenyls and divinylnaphthalenes.

The softening point of the phenolic resins is normally 40-200° C., preferably 60-150° C. When a phenolic resin with a softening point lower than this is used as a curing agent of epoxy resins, the epoxy resins cure into a product with reduced heat resistance. A phenolic resin with a softening point higher than this shows poorer miscibility with indole reins.

A phenolic resin composition is obtained from a phenolic resin and indole resin by melt mixing or solution mixing; that is, the two resins are mixed uniformly at a temperature higher than the softening temperature of one of the two by agitating or kneading or the two resins are dissolved respectively in a solvent and the resulting solutions are mixed uniformly by agitating or kneading. Solvents useful for solution mixing include alcohols such as methanol, ethanol, propanol, butanol, ethylene glycol, Methyl Cellosolve and Ethyl Cellosolve, ketones such as acetone, methyl ethyl ketone and methyl isobutyl ketone, ethers such as dimethyl ether, diethyl ether, diisopropyl ether, tetrahydrofuran and dioxane and aromatic solvents such as benzene, toluene, xylene, chlorobenzene and dichlorobenzene. It is possible to formulate this resin composition by incorporating epoxy resins, inorganic fillers, other phenolic resins and other additives.

This phenolic resin composition can be cured by hexamethylenetetramine which is a curing agent commonly used for phenolic resin molding materials. Moreover, it can be used as a curing agent for epoxy resins.

An epoxy resin composition formulated from the indole resins of this invention and epoxy contains at least epoxy resins and a curing agent and the indole resins are incorporated as a part or the whole of the curing agent. The amount of indole resins is normally 2-200 parts by weight, preferably 5-80 parts by weight, per 100 parts by weight of epoxy resins. Indole reins incorporated in an amount less than this improve little the moisture absorption, adhesion and fire retardance while indole resins incorporated in an amount more than this deteriorate the moldability and strength of cured product.

When the indole reins of this invention are used as the sole curing agent, they are incorporated in an amount that is usually decided in consideration of a balance of equivalent weight between >NH in the indole resins and epoxy group in the epoxy resins. The ratio of epoxy resin to curing agent in equivalent weight is normally in the range of 0.2-5.0, preferably 0.5-2.0. A ratio larger or smaller than this deteriorates the curability of epoxy resin compositions and also the heat resistance, mechanical strength and the like of the cured products.

To cure this epoxy resin composition, the indole resins of this invention can be used together with other curing agents. The amount of such other curing agents is set within such a range as to keep the amount of indole resins normally in the range of 2-200 parts by weight, preferably 5-80 parts by weight, per 100 parts by weight of epoxy resins. Indole resins incorporated less than this produce a small effect for reducing moisture absorption and improving adhesion and fire retardance while indole resins incorporated more than this deteriorate the moldability and the strength of the cured products.

Curing agents other than the indole resins include all the curing agents generally known for epoxy resins, for example, dicyandiamide, acid anhydrides, polyhydric phenols and aromatic and aliphatic amines. Of these curing agents, polyhydric phenols are preferable in applications such as encapsulants of semiconductors where a high degree of electrical insulation is required. Examples of curing agents are shown below.

Curing agents based on acid anhydrides include phthalic anhydride, tetrahydrophthalic anhydride, methyltetrahydrophthalic anhydride, hexahydrophthalic anhydride, methylhexahydrophthalic anhydride, methylhimic anhydride, dodecenylsuccinic anhydride, nadic anhydride and trimellitic anhydride.

Curing agents based on polyhydric phenols include dihydric phenols such as bisphenol A, bisphenol F, bisphenol S, fluorenebisphenol, 4,4'-biphenol, 2,2'-biphenol, hydroquinone, resorcin and naphthalenediol and trihydric or higher phenols such as tris(4-hydroxyphenyl)methane, 1,1,2,2-tetrakis(4-hydroxyphenyl)ethane, phenol novolac, o-cresol novolac, naphthol novolac and poly(vinyl phenol). They further include polyhydric phenolic compounds synthesized from phenols, naphthols and dihydric phenols such as bisphenol A, bisphenol F, bisphenol S, fluorenebisphenol, 4,4'-biphenol, 2,2'-biphenol, hydroquinone, resorcin and naphthalenediol and condensing agents such as formaldehyde, acetaldehyde, benzaldehyde, p-hydroxybenzaldehyde and p-xylylene glycol. The aforementioned phenolic resin composition of this invention can also be incorporated as a curing agent.

Curing agents based on amines include aromatic amines such as 4,4'-diaminodiphenylmethane, 4,4'-diaminodiphenylpropane, 4,4'-diaminodiphenyl sulfone, m-phenylenediamine and p-xylylenediamine and aliphatic amines such as ethylenediamine, hexamethylenediamine, diethylenetriamine and triethylenetetramine.

One kind or a mixture of two kinds or more of these curing agents is used for this epoxy resin composition.

Epoxy resins to be used in formulating this epoxy resin composition are selected from compounds possessing two or more epoxy groups in the molecule; for example, glycidyl ethers of dihydric phenols such as bisphenol A, bisphenol F, bisphenol S, fluorenebisphenol, 4,4'-biphenol, 2,2'-biphenol, tetrabromobisphenol A, hydroquinone and resorcine and glycidyl ethers of trihydric or higher phenolic compounds such as tris(4-hydroxyphenyl)methane, 1,1,2,2-tetrakis(4-hydroxyphenyl)ethane, novolacs derived from phenol, cresol and naphthol and phenol-aralkyl resins derived from phenol, cresol and naphthol. These epoxy resin may be used singly or as a mixture of two kinds or more.

It is allowable to incorporate oligomeric or polymeric polyesters, polyamides, polyimides, polyethers, polyurethanes, petroleum resins, indene resins, indene-coumarone resins and phenoxy resins as modifiers in this epoxy resin composition. Normally, 2-30 parts by weight of such oligomers or polymers is added to 100 parts by weight of epoxy resins.

Moreover, it is allowable to incorporate additives such as inorganic fillers, pigments, fire retardants, thixotropic agents, coupling agents, fluidity improvers and the like in this epoxy resin composition. Inorganic fillers include silica powder such as spherical or crushed fused silica and crystalline silica, alumina powder, glass powder, mica, talc, calcium carbonate, alumina and hydrated alumina and, when the composition is applied as an encapsulant of semiconductors, the inorganic filers are added in an amount of 70 wt % or more, preferably 80 wt % or more.

Pigments include organic or inorganic extender pigments and scaly pigments. Thixotropic agents include silicones, castor oil, aliphatic amide waxes, polyethylene oxide waxes and organic bentonites.

Furthermore, known curing accelerators such as amines, imidazoles, phosphines and Lewis acids may be used in curing of this epoxy resin composition as occasion demands. Concretely, they are tertiary amines such as 1,8-azabicyclo (5,4,0)undecene-7, triethylenediamine, benzyldimethylamine, triethanolamine, dimethylaminoethanol and tris(dimethylaminomethyl)phenol, imidazoles such as 2-methylimidazole, 2-phenylimidazole, 2-phenyl-4-methylimidazole and 2-heptadecylimidazole, phosphines such as tributylphosphine, methyldiphenylphosphine, triphenylphosphine, diphenylphosphine and phenylphosphine, tetra-substituted phosphonium tetra-substituted borates such as tetraphenylphosphonium tetraphenylborate, tetraphenylphosphonium ethyltriphenylborate and tetrabutylphosphonium tetrabutylborate and tetraphenylborates such as 2-ethyl-4-methylimidazole tetraphenylborate and N-methylmorpholine tetraphenylborate. The curing accelerator is added at a rate of 0.2-5 parts by weight per 100 parts by weight of epoxy resins.

The following additives may be further incorporated in case of need; mold release agents such as carnauba wax and OP Wax, coupling agents such as γ-glycidoxypropyltrimethoxysilane, colorants such as carbon black, fire retardants such as antimony trioxide, stress reducing agents such as silicone oil and lubricants such as calcium stearate.

This epoxy resin composition can be used in applications known to ordinary epoxy resin compositions such as encapsulants of semiconductors. In particular, prepreg can be prepared from this epoxy resin composition by dissolving it in an organic solvent to a state of varnish, impregnating fibrous materials such as glass cloth, Aramid nonwoven fabric and polyester nonwoven fabric with the varnish and removing the solvent. When necessary, the varnish may be applied to a material in the form of sheet such as a copper foil, stainless steel foil, polyimide film and polyester film.

This epoxy resin composition can be cured by heating and the resulting cured product shows excellent properties with respect to moisture absorption, heat resistance, adhesiveness, fire retardance and the like.

The epoxy resins of this invention represented by the general formula II can be prepared by reacting the indole reins represented by general formula I with epichlorohydrin. This reaction can be carried out in the same manner as an ordinary epoxidation reaction. An epoxy resin in which $R_1$ is glycidyloxy group can be prepared similarly from a hydroxyindole resin represented by the general formula I in which $R_1$ is OH.

For example, the reaction is carried out by dissolving the aforementioned indole resin in an excess of epichlorohydrin and allowing the solution to react in the presence of an alkali metal hydroxide such as sodium hydroxide and potassium hydroxide at 20-150° C., preferably at 30-80° C., for 1-10 hours. The alkali metal hydroxide is used at a rate of 0.8-1.2 moles, preferably 0.9-1.0 mole, per 1 mole of the sum of the hydroxyl and N—H groups in the indole resin. Although epichlorohydrin is used in excess of the sum of the hydroxyl and N—H groups in the indole resin, it is used at a rate of 1.5-30 moles, preferably 2-15 moles, per 1 mole of the sum of the hydroxyl and N—H groups in the indole resin. Upon completion of the reaction, the excess epichlorohydrin is removed by distillation, the residue is dissolved in a solvent such as toluene and methyl isobutyl ketone and the solution is filtered, washed with water to remove inorganic salts and stripped of the solvent by distillation to give the target epoxy resin.

An epoxy resin composition in which the epoxy reins of this invention are incorporated epoxy resins and curing agents and comprises the epoxy resins represented by the general formula II as an essential ingredient.

In the cases where the epoxy resins represented by the general formula II are present as an essential ingredient, any curing agent known effective for epoxy resins can be used; for example, dicyandiamide, polyhydric phenols, acid anhydrides and aromatic and aliphatic amines. The indole reins represented by general formula I may also be used as a curing agent.

As for examples of the polyhydric phenols, acid anhydrides and aromatic and aliphatic amines, reference should be made to the earlier paragraphs describing the epoxy resin compositions in which the indole resins represented by general formula I are incorporated.

In addition to the epoxy resins of this invention represented by general formula I, other kinds of epoxy resins may be incorporated as an epoxy resin ingredient in this epoxy resin composition.

As for examples of such other kinds of epoxy resins, reference should be made to the earlier paragraphs describing the epoxy resin compositions in which the indole resins represented by general formula I are incorporated.

In the case of this epoxy resin composition, the epoxy resin represented by general formula II account for 5-100%, preferably 60-100%, of the entire epoxy resins.

It is allowable to incorporate suitably oligomeric or polymeric polyesters, polyamides, polyimides, polyethers, polyurethanes, petroleum resins, indene-coumarone resins and phenoxy resins in this epoxy resin composition. It is further allowable to incorporate additives such as inorganic fillers, pigments, fire retardants, thixotropic agents, coupling agents, fluidity improvers and the like in this epoxy resin composition.

The following additives may be further incorporated in case of need; mold release agents such as carnauba wax and OP Wax, coupling agents such as γ-glycidoxypropyltrimethoxysilane, colorants such as carbon black, fire retardants such as antimony trioxide, stress reducing agents such as silicone oil and lubricants such as calcium stearate.

Where necessary, known curing accelerators may be used; for example, amines, imidazoles, phosphines and Lewis acids. The curing accelerators are added at a rate of 0.2-5 parts by weight per 100 parts by weight of the epoxy resins.

As for examples of such fillers and pigments, reference should be made to the earlier paragraphs describing the epoxy resin compositions in which the indole resins represented by general formula I are incorporated.

This resin composition is cured by such molding process as casting, compression molding and transfer molding. The molding temperature is normally set in the range of 120-220° C.

PREFERRED EMBODIMENTS OF THE INVENTION

This invention is described below with reference to the examples. In the examples, % and part are respectively on a weight basis.

EXAMPLE 1

In a 500-ml three-necked separable flask fitted with a stirrer, a cooling tube and a nitrogen inlet tube were placed 200 g of indole, 22.3 g of 92% paraformaldehyde and 4.0 g of oxalic acid and the mixture was heated to 90° C. until a solution was formed while introducing nitrogen. Thereafter, the solution was heated to 150° C. with stirring and allowed to react at this temperature for 5 hours. Meanwhile, water formed by the reaction was removed from the system. The reaction mixture was then heated to 200° C. under reduced pressure to remove condensed water and the unreacted indole and 190 g of indole resin A was obtained.

Indole resin A thus obtained showed a softening point of 123° C. and a melt viscosity of 0.24 Pa·s at 150° C. The residual monomer measured by GPC was 0.1 wt %. The peaks read off the GPC chart indicate the formation of 45.0% of a compound corresponding to n =1, 30.2% of a compound corresponding to n=2, 13.7% of a compound corresponding to n =3 and 10.1% of compounds corresponding to n≧4 in general formula I. The infrared absorption spectrum and H-NMR spectrum are respectively shown in FIGS. 1 and 2.

Figure 1:
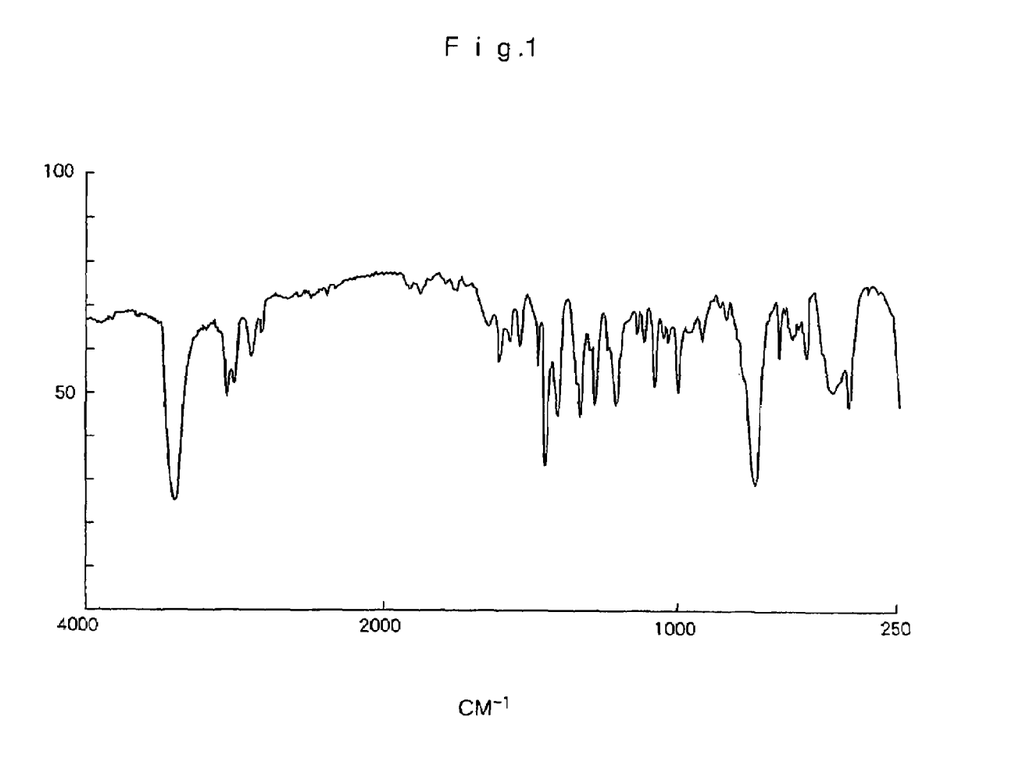
FIG. 1 is an infrared absorption spectrum of indole resin A of this invention and FIG. 2 is an H-NMR spectrum of indole resin A.
Figure 2:
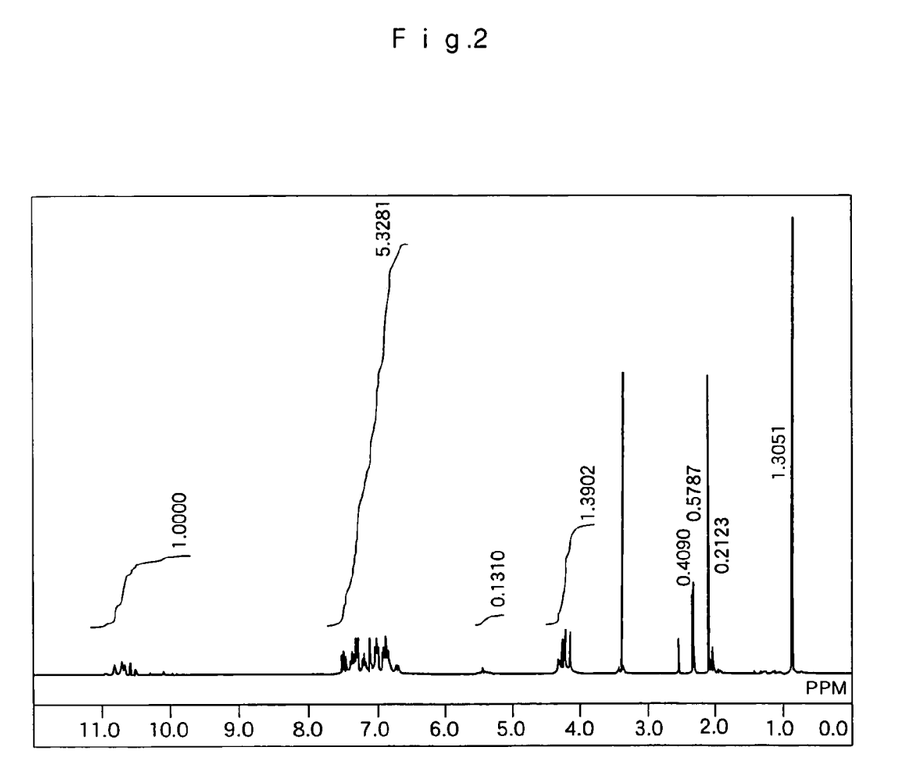

The viscosity was measured by an ICI cone-plate type viscometer while the softening point was measured in accordance with the ring and ball method specified by JIS K-6911. The GPC measurements were made under the following conditions: equipment, HLC-82A available from Tosoh Corporation; columns, TSK-GEL2000×3 and TSK-GEL4000× 1, both available from Tosoh Corporation; solvent, tetrahydrofuran; flow rate, 1 ml/min; temperature, 38° C.; detector, RI; calibration, polystyrene. The infrared absorption spectrum was measured by the use of a KBr tablet and the H-NMR spectrum was measured in dimethyl sulfoxide-d6 with the aid of JNM-GX400, an equipment available from JEOL (Japan Electron Optics Laboratory Co., Ltd).

EXAMPLE 2

The reaction was carried out as in Example 1 with the exception of using 27.9 g of 92% paraformaldehyde to give 194 g of indole resin B.

This resin showed a softening point of 104° C. and a melt viscosity of 0.8 Pa·s at 150° C. The residual monomer measured by GPC was 0.2 wt %. The peaks read off the GPC chart indicate the formation of 36.3% of a compound corresponding to n=1, 30.0% of a compound corresponding to n=2, 15.8% of a compound corresponding to n=3 and 17.1% of compounds corresponding to n≧4 in general formula I.

EXAMPLE 3

The reaction was carried out as in Example 1 with the exception of using 33.5 g of 92% paraformaldehyde to give 198 g of indole resin C. This resin showed a softening point of 93° C. and a melt viscosity of 7.0 Pa·s at 150° C. The residual monomer measured by GPC was 0.3 wt %. The peaks read off the GPC chart indicate the formation of 24.8% of a compound corresponding to n=1, 28.0% of a compound corresponding to n=2, 17.9% of a compound corresponding to n=3 and 29.1% of compounds corresponding to n≧4 in general formula I.

EXAMPLE 4

In a 500-ml three-necked separable flask fitted with a stirrer, a cooling tube and a nitrogen inlet tube were placed 200 g of indole and 75 g of p-xylylene dichloride and the mixture was heated to 90° C. until a solution was formed while introducing nitrogen. Thereafter, the solution was heated to 120° C. with stirring and allowed to react at this temperature for 4 hours. Meanwhile, hydrochloric acid formed by the reaction was removed from the system. The reaction mixture was then heated to 200° C. under reduced pressure to remove the unreacted indole and 128 g of indole resin D, dark brown in color, was obtained. This resin showed a softening point of 90° C. and a melt viscosity of 0.3 Pa·s at 150° C.

The residual monomer measured by GPC was 0.2 wt %. The peaks read off the GPC chart indicate the formation of 51.4% of a compound corresponding to n=1, 27.3% of a compound corresponding to n=2, 13.4% of a compound corresponding to n=3 and 7.7% of compounds corresponding to n≧4 in general formula I.

EXAMPLE 5

To 100 g of phenol novolac melted and kept at 150° C. was added 100 g of the indole resin obtained in Example 1 and melted uniformly to give 200 g of a phenolic resin composition with a softening point of 97° C. and a melt viscosity of 4.6 Pa·s at 150° C.

EXAMPLES 6-13 AND COMPARATIVE EXAMPLES 1-2

Epoxy resin compositions were prepared by kneading o-cresol novolac type epoxy resin (EOCN; epoxy equivalent 200, softening point 70° C.) as an epoxy resin ingredient, the indole resins obtained in Examples 1-4 (resin A, B, C and D), the phenolic resin composition (PRC-A) obtained in Example 5, phenol novolac (curing agent A; hydroxyl equivalent 103, softening point 82° C.) and phenol-aralkyl resin (curing agent B or XL-225-LL available from Mitsui Chemicals, Inc.; hydroxyl equivalent 172, softening point 74° C.) as curing agents, silica (average particle diameter, 22 µm) as a filler and triphenylphosphine as a curing accelerator according to the formulation shown in Table 1. These epoxy resin compositions were molded at 175° C. and poured at 175° C. for 12 hours and the test specimens prepared from the cured products were used for measuring a variety of properties.

The glass transition temperature (Tg) was measured with the aid of a thermomechanical analyzer at a rate of temperature rise of 10° C./min. The water absorption was measured by molding respective epoxy rein composition into a disk with a diameter of 50 mm and a thickness of 3 mm, postcuring the disk and allowing the disk to absorb moisture at 133° C. and 3 atm for 96 hours. The adhesiveness was evaluated by compression-molding respective epoxy resin composition on a copper foil at 175° C., postcuring at 175° C. for 12 hours and measuring the peel strength. The fire retardance was evaluated by molding respective epoxy resin composition into a test specimen with a thickness of 1/16 inch and measuring the sum of burning time of five test specimens in accordance with UL94V-0. The formulation and the test results are respectively shown in Tables 1 and 2.

TABLE 1

|  | Example | | | | | | | | Comparative example | |
| --- | --- | --- | --- | --- | --- | --- | --- | --- | --- | --- |
|  | 6 | 7 | 8 | 9 | 10 | 11 | 12 | 13 | 1 | 2 |
| EOCN | 95.7 | 96.8 | 97.9 | 95.2 | 84.0 | 82.6 | 92.3 | 87.5 | 99.0 | 80.6 |
| Resin A | 28.7 | — | — | — | — | 24.8 | — | — | — | — |
| Resin B | — | 19.4 | — | — | 16.8 | — | 57.7 | — | — | — |

TABLE 1-continued

|  | Example | | | | | | | | Comparative example | |
| --- | --- | --- | --- | --- | --- | --- | --- | --- | --- | --- |
|  | 6 | 7 | 8 | 9 | 10 | 11 | 12 | 13 | 1 | 2 |
| Resin C | — | — | — | — | — | — | — | — | — | — |
| Resin D | — | — | — | — | — | — | — | 17.5 | — | — |
| PRC-A | — | — | 9.8 | 54.7 | — | — | — | — | — | — |
| Curing agent A | 25.6 | 33.9 | 50.4 | — | — | 42.5 | — | 45.1 | 51.0 | — |
| Curing agent B | — | — | — | — | 49.1 | — | — | — | — | 69.3 |
| Silica | 450 | 450 | 450 | 450 | 450 | 450 | 450 | 450 | 450 | 450 |
| Curing accelerator | 1.5 | 1.5 | 1.5 | 1.5 | 1.5 | 1.5 | 1.5 | 1.5 | 1.5 | 1.5 |

TABLE 2

|  | Example | | | | | | | | Comparative example | |
| --- | --- | --- | --- | --- | --- | --- | --- | --- | --- | --- |
|  | 6 | 7 | 8 | 9 | 10 | 11 | 12 | 13 | 1 | 2 |
| Tg (° C.) | 146 | 154 | 160 | 135 | 133 | 139 | 141 | 143 | 165 | 128 |
| Thermal expansion coefficient (<Tg, ×$10^{-5}$) | 1.6 | 1.6 | 1.6 | 1.6 | 1.6 | 1.6 | 1.5 | 1.6 | 1.6 | 1.7 |
| Thermal expansion coefficient (>Tg, ×$10^{-5}$) | 6.2 | 6.1 | 6.1 | 6.2 | 6.3 | 6.4 | 6.1 | 6.3 | 6.1 | 6.6 |
| Flexural strength (MPa) | 144 | 141 | 145 | 147 | 143 | 146 | 141 | 145 | 144 | 142 |
| Flexural modulus (GPa) | 16.8 | 16.7 | 16.8 | 17.2 | 17.1 | 17.1 | 16.3 | 16.1 | 16.8 | 16.4 |
| Adhesive strength (kgf) | 93 | 85 | 62 | 108 | 123 | 139 | 164 | 141 | 38 | 45 |
| Water absorption (wt %) | 0.23 | 0.24 | 0.27 | 0.24 | 0.21 | 0.27 | 0.21 | 0.26 | 0.34 | 0.28 |
| Burning time (sec) | 8 | 19 | 28 | 5 | 5 | 6 | 0 | 11 | 360 | 140 |

EXAMPLE 14

In a 500-ml three-necked separable flask fitted with a stirrer, a cooling tube and a nitrogen inlet tube were placed 200 g of indole, 16.7 g of 92% paraformaldehyde and 2.2 g of oxalic acid and the mixture was heated to 90° C. until a solution was formed while introducing nitrogen. Thereafter, the solution was heated to 150° C. with stirring and allowed to react at this temperature for 5 hours. Meanwhile, water formed by the reaction was removed from the system. The reaction mixture was then heated to 200° C. under reduced pressure to remove condensed water and the unreacted indole and 130 g of indole resin E was obtained. Indole resin E thus obtained showed a softening point of 84° C. and a melt viscosity of 0.08 Pa·s at 150° C. The indole oligomers consisted of 58.2% of dimers, 28.1% of trimers, 8.9% of tetramers and 4.6% of pentamers and higher polymers when measured by GPC. The residual monomer was 0.1 wt %.

EXAMPLE 15

In a 500-ml three-necked separable flask fitted with a stirrer, a cooling tube and a nitrogen inlet tube were placed 351 g of indole and 100 g of methanol and the mixture was heated to 80° C. until a solution was formed while introducing nitrogen. Thereafter, 25.0 g of a 37% aqueous solution of formaldehyde was added in drops to the solution with stirring and the mixture was heated to 150° C. and allowed to react at this temperature for 7 hours. Meanwhile, water formed by the reaction was removed from the system. The reaction mixture is then heated to 200° C. under reduced pressure to remove condensed water and the unreacted indole and 70 g of indole resin F mainly consisting of indole dimers was obtained. Indole resin F showed a softening point of 159-161° C. after recrystallization from isopropyl alcohol and the content of indole dimers (n=1) measured by GPC was 98.0%.

EXAMPLE 16

In a 500-ml three-necked separable flask fitted with a stirrer, a cooling tube and a nitrogen inlet tube were placed 200 g of indole and 90 g of p-xylylene dichloride and the mixture was heated to 90° C. until a solution was formed while introducing nitrogen. Thereafter, the solution was heated to 120° C. and allowed to react at this temperature for 4 hours. Meanwhile, hydrochloric acid formed by the reaction was removed from the system. The reaction mixture is then heated to 200° C. under reduced pressure to remove the unreacted indole and 153 g of indole resin G, dark brown in color, was obtained.

Indole resin G showed a softening point of 98° C. and a melt viscosity of 0.84 Pa·s at 150° C. The residual monomer measured by GPC was 0.1 wt %. The peaks read off the GPC chart indicate formation of 40.1% of a compound corresponding to n=1, 23.3% of a compound corresponding to n=2, 14.5% of a compound corresponding to n=3 and 13.6% of compounds corresponding to n≧4.

EXAMPLE 17

In 700 g of epichlorohydrin was dissolved 100 g of indole resin E prepared in Example 14 and then 18.3 g of benzyl-triethylammonium chloride was added. Thereafter, 470 g of a 48% aqueous solution of potassium hydroxide was added in drops at 25° C. with stirring over 3 hours and the reaction was allowed to continue for another 1 hour after completion of the dropwise addition. Upon completion of the reaction, salts formed by the reaction were removed by filtration, the reaction mixture was washed with water, the epichlorohydrin was distilled off and 125 g of epoxy resin (epoxy resin A) was obtained.

Figure 3:
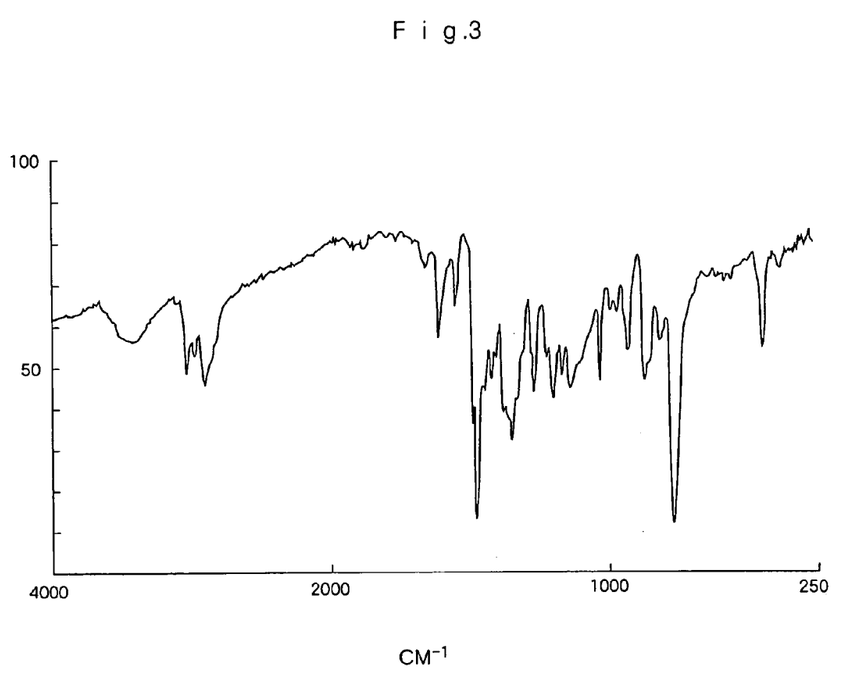
FIG. 3 is an infrared absorption spectrum of epoxy resin A of this invention and FIG. 4 is an H-NMR spectrum of epoxy resin A.
Figure 4:
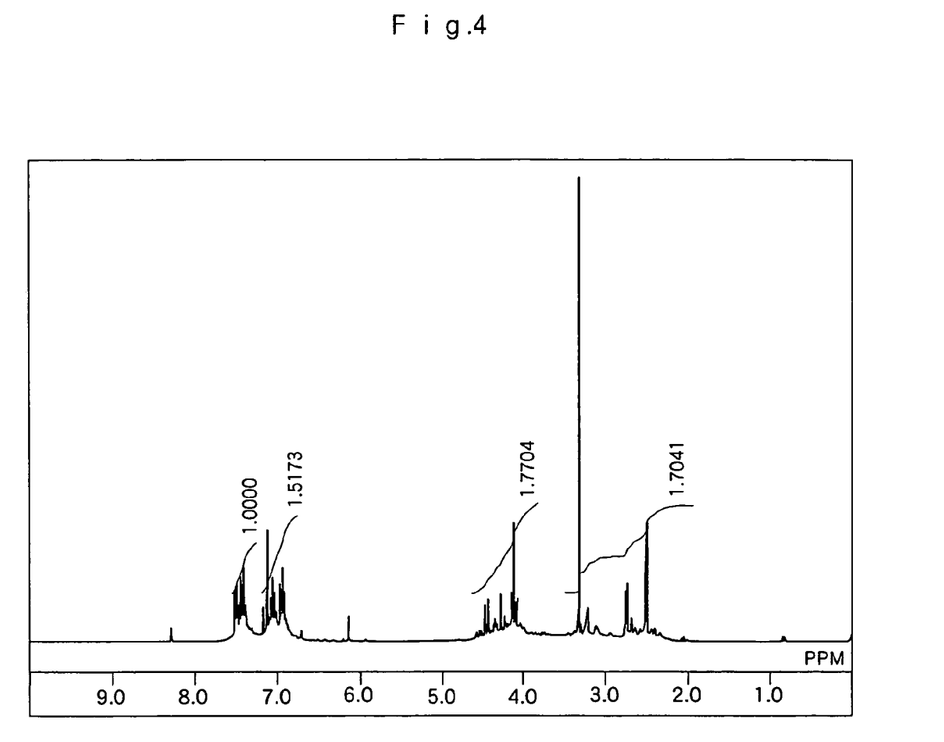

Epoxy resin A showed a softening point of 88° C., a melt viscosity of 1.08 Pa·s and an epoxy equivalent of 220. The peaks read off the GPC chart indicate formation of 38.1% of a compound corresponding to n=1, 24.8% of a compound corresponding to n=2, 16.2% of a compound corresponding to n=3 and 20.9% of compounds corresponding to n≧4. It is to be understood that the number n of epoxy resin read off the GPC chart is equal to the number of indole rings in the compound minus 1 as a polymer formed by the ring-opening reaction of epoxy group is counted simultaneously. The IR spectrum and H-NMR spectrum of this resin are respectively shown in FIGS. 3 and 4.

EXAMPLE 18

In 700 g of epichlorohydrin and 140 g of diglyme was dissolved 100 g of the indole dimer obtained in Example 15. Thereafter, 80.6 g of 99% sodium hydroxide and 5.0 g of pure water were added and the mixture was heated to 120° C. and allowed to react at this temperature for 10 hours. Meanwhile, water formed by the reaction was removed from the system. Upon completion of the reaction, salts formed by the reaction were filtered off, the reaction mixture was washed with water, the epichlorohydrin was distilled off and 87 g of epoxy resin B was obtained. This resin showed a softening point of 45° C., a melt viscosity of 0.03 Pa·s and an epoxy equivalent of 216.

EXAMPLE 19

In 700 g of epichlorohydrin was dissolved 100 g of indole resin G obtained in Example 16 and then 3 g of benzyltriethylammonium chloride was added. Thereafter, 150 g of a 48% aqueous solution of sodium hydroxide was added in drops at 25° C. with stirring over 3 hours and the reaction was allowed to continue for another 1 hour after completion of the dropwise addition. Upon completion of the reaction, salts formed by the reaction were filtered off, the reaction mixture was washed with water, the epichlorohydrin was distilled off and 126 g of epoxy resin C was obtained. This resin showed a softening point of 74° C., a melt viscosity of 0.31 Pa·s and an epoxy equivalent of 230.

EXAMPLES 20-25 AND COMPARATIVE EXAMPLES 3-5

Epoxy resin compositions were prepared in accordance with the formulation shown in Table 3 from epoxy resins A, B and C synthesized in Examples 17-19, o-cresol novolac type epoxy resin (epoxy resin D or EOCN-1020-65 available from Nippon Kayaku Co., Ltd.; epoxy equivalent 200, hydrolyzable chlorine content 400 ppm, softening point 65° C.), biphenyl type epoxy resin (epoxy resin E or YX4000HK available from Yuka Shell Epoxy Kabushiki Kaisha; epoxy equivalent 195, hydrolyzable chlorine content 450 ppm, melting point 105° C.) as an epoxy resin ingredient, indole resin E synthesized in Example 14, phenol novolac (curing agent C or PSM-4261 available from Gun Ei Chemical Industry Co., Ltd.; hydroxyl equivalent 103, softening point 80° C.) and 1-naphthol-aralkyl type resin (curing agent D or SN-475 available from Nippon Steel Chemical Co., Ltd.; hydroxyl equivalent 210, softening point 77° C.) as a curing agent, spherical silica (average particle diameter, 18 μm) as a filler and triphenylphosphine as a curing accelerator. The numerical values in Table 3 are expressed in part by weight.

These epoxy resin compositions were molded at 175° C. and postcured at 175° C. for 12 hours and the test specimens prepared from the cured products were used for measuring a variety of properties. The results are shown in Table 4.

The linear expansion coefficient was determined with the aid of a thermomechanical analyzer at a rate of temperature rise of 10° C./min. The water absorption was determined by preparing a test specimen, 50 mm in diameter and 3 mm in thickness, allowing the specimen to absorb moisture at 85° C. and 85% RH for 100 hours and finding the rate of change in weight. The adhesive strength was evaluated by placing respective epoxy resin composition between two copper foils, compression molding at 175° C. to an article measuring 25 mm×12.5 mm×0.5 mm, postcuring the molded article at 180° C. for 12 hours and measuring the tensile shear strength. Other measurements were made under the same conditions as in Examples 6-13.

TABLE 3

|  | Example | | | | | | Comparative example | | |
| --- | --- | --- | --- | --- | --- | --- | --- | --- | --- |
|  | 20 | 21 | 22 | 23 | 24 | 25 | 3 | 4 | 5 |
| Epoxy resin A | 102.0 | 76.5 | 85.0 | 88.5 |  |  |  |  |  |
| Epoxy resin B |  |  |  |  | 76.0 |  |  |  |  |
| Epoxy resin C |  |  |  |  |  | 94.5 |  |  |  |
| Epoxy resin D |  |  |  |  |  |  | 99.0 | 73.0 |  |
| Epoxy resin E |  |  |  |  |  |  |  |  | 72.0 |
| Indole resin E |  |  | 22.1 | 20.0 |  |  |  |  |  |
| Curing agent C | 47.8 |  |  | 41.4 |  | 55.3 | 51.0 |  |  |
| Curing agent D |  | 73.0 | 43.2 |  | 73.9 |  |  | 76.7 | 77.5 |
| Spherical silica | 800 | 800 | 800 | 800 | 800 | 800 | 800 | 800 | 800 |
| Curing accelerator | 1.2 | 1.2 | 1.2 | 1.2 | 1.2 | 1.2 | 1.2 | 1.2 | 1.2 |
| Carbon black | 5 | 5 | 5 | 5 | 5 | 5 | 5 | 5 | 5 |
| Carnauba wax | 3 | 3 | 3 | 3 | 3 | 3 | 3 | 3 | 3 |
| Content of silica (wt %) | 83 | 83 | 83 | 83 | 83 | 83 | 83 | 83 | 83 |

TABLE 4

|  | Example | | | | | | Comparative example | | |
|---|---|---|---|---|---|---|---|---|---|
|  | 20 | 21 | 22 | 23 | 24 | 25 | 3 | 4 | 5 |
| Spiral flow (cm) | 78 | 68.5 | 62 | 73 | 98 | 63 | 73 | 66 | 89 |
| Gel time (sec) | 30 | 25 | 23 | 25 | 26 | 33 | 31 | 31 | 32 |
| Hardenss when heated | 74 | 71 | 70 | 67 | 64 | 71 | 77 | 67 | 62 |
| Thermal expansion coefficient ($\times 10^{-5}$) (<Tg) | 1.0 | 1.0 | 1.0 | 1.0 | 1.0 | 1.0 | 1.1 | 1.1 | 1.1 |
| (>Tg) | 3.9 | 3.8 | 3.7 | 3.9 | 3.8 | 3.9 | 4.2 | 4.0 | 4.1 |
| Tg (° C.) | 168 | 146 | 141 | 147 | 139 | 145 | 163 | 142 | 124 |
| Flexural strength (MPa) | 180 | 184 | 172 | 181 | 171 | 177 | 174 | 168 | 166 |
| Flexural modulus (GPa) | 22.2 | 22.3 | 22.5 | 22.2 | 22.2 | 22 | 21.3 | 21.0 | 21.0 |
| Water absorption (wt %, 100 h) | 0.21 | 0.17 | 0.15 | 0.16 | 0.15 | 0.2 | 0.27 | 0.23 | 0.21 |
| Adhesive strength (MPa) | 2.1 | 2.4 | 2.6 | 2.5 | 3.2 | 2.8 | 1.2 | 1.5 | 1.7 |
| Burning time (sec) | 65 | 32 | 14 | 38 | 21 | 18 | >300 *1 | 190 | 225 |

*1 The flame reached the upper end of the test specimen without self extinguishing in all the test specimens.

INDUSTRIAL APPLICABILITY

The indole resins of this invention are useful as intermediates and cure agents for epoxy resins. Epoxy resin compositions comprising the indole resins cure with excellent heat resistance, moisture resistance, fire retardance and adhesiveness to materials of different kind and they can be used for applications such as encapsulants of electric and electronic parts and materials for circuit boards. Moreover, epoxy resin compositions comprising the epoxy resins of this invention cure with excellent fire retardance, adhesiveness, moisture resistance and heat resistance and they can be used in such applications as laminating, molding, casting and adhesion.

What is claimed is:

1. Epoxy resins being represented by the following general formula II wherein $R_1$ is hydrogen, hydrocarbon group containing 1-8 carbon atoms, alkoxy group containing 1-6 carbon atoms, glycidyloxy group or halogen, X is a crosslinking group represented by general formula (a) or (b)

(wherein $R_2$ and $R_3$ are hydrogen or hydrocarbon group containing 1-6 carbon atoms, $R_4$ and $R_5$ are hydrogen or methyl group and m is 1 or 2), n is an integer of 1-20 and G is glycidyl group.

2. Epoxy resin compositions comprising epoxy resins and curing agents as essential ingredients wherein the epoxy resins described in claim 1 account for a part or the whole of the epoxy resin ingredient.

3. Cured products of the epoxy resin compositions described in claim 2.

4. Epoxy resins as described in claim 1 which is obtained by reacting indole resins with epichiorohydrin in the presence of an alkali metal hydroxide, said indole resins being represented by the following general formula I wherein $R_1$ is hydrogen, hydroxyl group, hydrocarbon group containing 1-8 carbon atoms, alkoxy group containing 1-6 carbon atoms or halogen, X is a crosslinking group represented by the following general formula (a) or (b)

(wherein $R_2$ and $R_3$ are hydrogen or hydrocarbon group containing 1-6 carbon atoms, $R_4$ and $R_5$ are hydrogen or methyl group and m is 1 or 2) and n is an integer of 1-20 .

II (a)

(b)

5. Epoxy resin compositions comprising epoxy resins and curing agents as essential ingredients wherein the epoxy resins described in claim 4 account for a part or the whole of the epoxy resin ingredient.

6. Cured products of the epoxy resin compositions described in claim 5.

* * * * *